(12) United States Patent
Rolfe et al.

(10) Patent No.: US 11,547,804 B2
(45) Date of Patent: Jan. 10, 2023

(54) ADJUSTABLE CLOCK FREQUENCY IN AN INJECTOR HEAD ASSEMBLY FOR AN MRI SYSTEM

(71) Applicant: ACIST Medical Systems, Inc., Eden Prairie, MN (US)

(72) Inventors: Steven Mark Guy Rolfe, Lausanne (CH); Volker Kremer, Eschweiler (DE); Eckhard Buchholtz, Eschweiler (DE); Michael Van De Bruck, Eschweiler (DE); Gunter Bruckmann, Eschweiler (DE)

(73) Assignee: ACIST MEDICAL SYSTEMS, INC., Eden Prairie, MN (US)

( * ) Notice: Subject to any disclaimer, the term of this patent is extended or adjusted under 35 U.S.C. 154(b) by 392 days.

(21) Appl. No.: 16/956,424

(22) PCT Filed: Dec. 19, 2018

(86) PCT No.: PCT/EP2018/085994
§ 371 (c)(1),
(2) Date: Jun. 19, 2020

(87) PCT Pub. No.: WO2019/122018
PCT Pub. Date: Jun. 27, 2019

(65) Prior Publication Data
US 2021/0085886 A1    Mar. 25, 2021

(30) Foreign Application Priority Data
Dec. 20, 2017 (EP) ..................................... 17208916

(51) Int. Cl.
*A61M 5/315* (2006.01)
*A61B 5/055* (2006.01)
(Continued)

(52) U.S. Cl.
CPC ......... *A61M 5/31546* (2013.01); *A61B 5/055* (2013.01); *A61M 5/007* (2013.01);
(Continued)

(58) Field of Classification Search
None
See application file for complete search history.

(56) References Cited

U.S. PATENT DOCUMENTS

| 5,494,036 A | 2/1996 | Uber, III et al. | |
|---|---|---|---|
| 6,621,433 B1 * | 9/2003 | Hertz | G01R 33/3621 324/309 |
| 2003/0058502 A1 * | 3/2003 | Griffiths | G01R 33/283 398/139 |

(Continued)

FOREIGN PATENT DOCUMENTS

WO    2019122018 A1    6/2019

OTHER PUBLICATIONS

Russian Patent Office, "Official Action", from PCT Application No. PCT/EP2018/085994, dated Dec. 27, 2021 from Foreign Counterpart to U.S. Appl. No. 16/956,424, pp. 1 through 14, Published: RU.

(Continued)

*Primary Examiner* — Tahmina N Ansari
(74) *Attorney, Agent, or Firm* — Volpe Koenig

(57) ABSTRACT

An MRI system (100) is proposed (for generating one or more images of a body-part of a patient under analysis); the MRI system (100) comprises an injector head assembly (155), for injecting at least one medical fluid into the patient, having a clock unit (340) for providing a clock signal with a clock frequency. The MRI system (100) comprises means (420-425; 445-460) for adjusting the clock frequency in response to a manual command and/or to a detection of a degradation of the images. An injector system (155,165) for use in this MRI system (100) is also proposed. Moreover, a corresponding method (500) for managing the injector head
(Continued)

assembly (155) is proposed. A computer program (400) for implementing the method (500) and a corresponding computer program product are also proposed.

29 Claims, 6 Drawing Sheets

(51) Int. Cl.
*G01R 33/54* (2006.01)
*G16H 30/20* (2018.01)
*G16H 40/63* (2018.01)
*A61M 5/00* (2006.01)
*G01R 33/56* (2006.01)
*G01R 33/20* (2006.01)
*A61M 5/19* (2006.01)

(52) U.S. Cl.
CPC .......... *G01R 33/20* (2013.01); *G01R 33/546* (2013.01); *G01R 33/5608* (2013.01); *G16H 30/20* (2018.01); *G16H 40/63* (2018.01); *A61M 5/19* (2013.01); *A61M 2205/3331* (2013.01); *A61M 2205/52* (2013.01)

(56) References Cited

U.S. PATENT DOCUMENTS

2016/0161578 A1* 6/2016 Weissler ................ G01R 33/36
 324/309
2021/0085886 A1* 3/2021 Rolfe ..................... G01R 33/20

OTHER PUBLICATIONS

Gebhardt et al., "FPGA-based RF interference reduction techniques for simultaneous PET-MRI", Physics in Medicine & Biology 61, 2016, pp. 3500-3526, Institute of Physics and Engineering in Medicine.

International Searching Authority, "International Search Report and Written Opinion from PCT Application No. PCT/EP2018/085994", dated Mar. 25, 2019, pp. 1 through 17, Published: WO.

* cited by examiner

ADJUSTABLE CLOCK FREQUENCY IN AN INJECTOR HEAD ASSEMBLY FOR AN MRI SYSTEM

This application claims priority to International Patent Application No. PCT/EP2018/085994 filed on Dec. 19, 2018, which claims priority to EP Patent Application No. 17208916.1 filed on Dec. 20, 2017.

TECHNICAL FIELD

The present disclosure relates to the medical field. More specifically, this disclosure relates to Magnetic Resonance Imaging (MRI).

BACKGROUND ART

The background of the present disclosure is hereinafter introduced with the discussion of techniques relating to its context. However, even when this discussion refers to documents, acts, artefacts and the like, it does not suggest or represent that the discussed techniques are part of the prior art or are common general knowledge in the field relevant to the present disclosure.

MRI is a well-established technique that is routinely used in medical imaging applications (for example, for diagnostic/therapeutic purposes). Particularly, the MRI technique allows acquiring visual representations (images) of body-parts inside corresponding patients (and then hidden by their skin) in a substantially non-invasive manner (i.e., without performing any surgery actions).

In general terms, the MRI technique is based on the exposure of a body area under analysis to a high magnetic field. As each body-part reacts to the magnetic field in a different way according to its morphological and/or physiological structure, by measuring a response of the body-part to the magnetic field it is possible to infer corresponding characteristics of the body-part (which may be used to create its images).

Preferably, one or more medical fluids are administered to each patient during his/her analysis. For example, a contrast agent (or contrast media) may be administered, possibly along with a saline solution, to enhance the response of a corresponding target feature, i.e., a structure with specific characteristics (such as a known lesion). The contrast agent then makes any portions of the body-part with this target feature more conspicuous in the corresponding images. As a result, the target feature (which might otherwise be hardly distinguishable from other nearby structures, for example, surrounding tissues) is highlighted in the images. This significantly facilitates the task of health care professionals (HCPs), and particularly the identification and/or characterization of lesions, the monitoring of their evolution or response to medical treatments.

The contrast agent is usually administered to the patient by injection. For this purpose, an (automated) injector system may be used. The injector system pressurizes the contrast agent and injects it into the patient under predetermined injection conditions (for example, at a specific flow rate and volume). In this way, the contrast agent may be injected in a controlled, safe and efficient manner.

Any MRI system has a high sensitivity to disturbing factors that might adversely affect its operation. Therefore, an injector head assembly of the injector system (to be placed necessarily close to the patient during his/her analysis) is resistant to magnetic fields and substantially MR conditional, i.e., it is designed to avoid, or at least largely attenuate, any known cause of interference with the operation of the MRI system.

Nevertheless, in very specific situations the injector head assembly may cause degradation of the images; particularly, the images may be blemished by artefacts in the form of anomalous lines crossing them (with some portions of the body-parts that also fade or disappear). These artefacts may appear after a relatively long lifetime of the injector head assembly. Moreover, the artefacts are highly sporadic; particularly, an incidence of the artefacts in the images changes under different operative conditions of the MRI system (for example, position of the injector head assembly, room temperature).

Therefore, the identification of a cause of the artefacts and its removal is challenging. Particularly, it is very difficult (if not impossible) to reproduce the artefacts during a design phase of the injector system. Moreover, generally it is not possible to track the operative conditions under which the artefacts appear in the field. In any case, the injector system may be used with a number of different MRI systems, most of them having operative characteristics that are mainly not publicly available.

All of the above may adversely affect a quality of the images and it may cause misinterpretations in the analyses of the corresponding body-parts (and then in the diagnosis/therapy of possible lesions thereof). Moreover, this is quite disturbing for the health care professionals and it may cause corresponding complaints (with a negative effect on a corresponding customer satisfaction).

SUMMARY

A simplified summary of the present disclosure is herein presented in order to provide a basic understanding thereof; however, the sole purpose of this summary is to introduce some concepts of the disclosure in a simplified form as a prelude to its following more detailed description, and it is not to be interpreted as an identification of its key elements nor as a delineation of its scope.

In general terms, the present disclosure is based on the idea of adjusting a clock frequency of the injector head assembly in an operative condition of the MRI system.

Particularly, an aspect provides an MRI system (for generating one or more images of a body-part of a patient under analysis); the MRI system comprises an injector head assembly (for injecting at least one medical fluid into the patient) having a clock unit for providing a clock signal with a clock frequency. The MRI system comprises means for adjusting the clock frequency in response to a manual command and/or to a detection of a degradation of the images.

A further aspect provides an injector system for use in the MRI system.

A further aspect provides a corresponding method for managing the injector head assembly.

A further aspect provides a computer program for implementing the method.

A further aspect provides a corresponding computer program product.

More specifically, one or more aspects of the present disclosure are set out in the independent claims and advantageous features thereof are set out in the dependent claims, with the wording of all the claims that is herein incorporated verbatim by reference (with any advantageous feature provided with reference to any specific aspect that applies mutatis mutandis to every other aspect).

BRIEF DESCRIPTION OF THE DRAWINGS

The solution of the present disclosure, as well as further features and the advantages thereof, will be best understood with reference to the following detailed description thereof, given purely by way of a non-restrictive indication, to be read in conjunction with the accompanying drawings (wherein, for the sake of simplicity, corresponding elements are denoted with equal or similar references and their explanation is not repeated, and the name of each entity is generally used to denote both its type and its attributes, like value, content and representation). In this respect, it is expressly intended that the drawings are not necessary drawn to scale (with some details that may be exaggerated and/or simplified) and that, unless otherwise indicated, they are merely used to illustrate the structures and procedures described herein conceptually. Particularly.

DETAILED DESCRIPTION

Figure 1:
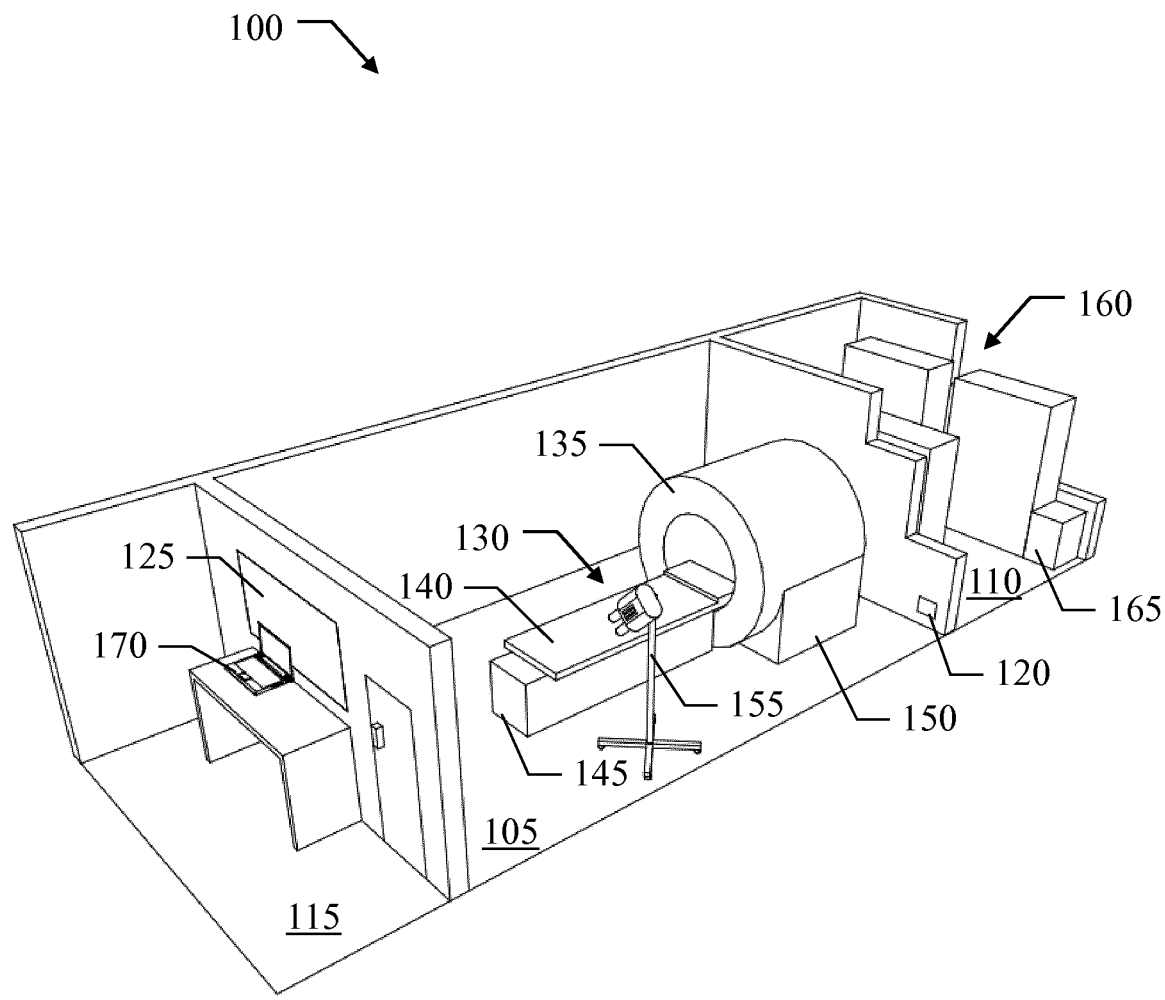
FIG. 1 shows a pictorial representation of an MRI system wherein the solution according to an embodiment of the present disclosure may be implemented.

With reference in particular to FIG. 1, a pictorial representation is shown of an MRI system 100 wherein the solution according to an embodiment of the present disclosure may be implemented.

The MRI system 100 is arranged at an MRI installation comprising a scanner room 105, an equipment room 110 and a control room 115. The scanner room 105 is used to shield the MRI system 100; particularly, the scanner room 105 implements a Radio-Frequency (RF) shielding (to block, or at least largely attenuate, RF radiations from outside that might adversely affect operation of the MRI system 100), a magnetic shielding (to block, or at least largely attenuate, any leakage of magnetic field from inside that might be harmful for persons) and an acoustic shielding (to block, or at least largely attenuate, transmission of noise from inside that might be disturbing for persons). The equipment room 110 is used to support operation of the MRI system 100; the equipment room 110 communicates with the scanner room 105 via a penetration panel 120 provided with RF-filters and waveguides (to avoid, or at least largely attenuate, any loss of shielding of the scanner room 105). The control room 115 is used to control operation of the MRI system 100 by dedicated health care professionals; the control room 115 is provided with a window 125 for visual inspection of the scanner room 105.

The MRI system 100 comprises the following components in the scanner room 105. An MRI scanner 130 comprises a gantry 135 (in the form of a hollow cylinder) with an opening for receiving a patient to be analyzed (not shown in the figure). The gantry 135 houses, not visible in the figure, a superconducting (or permanent) magnet (for generating a very high stationary magnetic field, for example, of the order of 1-9 T), multiple sets of gradient coils for different axes (coupled with the superconducting magnet for adjusting the stationary magnetic field) and an RF coil (with a specific structure, such as surface coil, saddle coil or Helmholts coil, for applying magnetic pulses to a corresponding type of body-part to be analyzed and for receiving corresponding response signals). The gantry 135 is provided with an RF/magnetic shield (not visible in the figure), which surrounds the superconducting magnet, the gradient coils and the RF coil to protect them from external interferences and to confine the magnetic field generated by them. The MRI scanner 130 comprises a table 140 for laying down the patient. The table 140 is mounted on a base 145, which is provided with a motor (not visible in the figure) for sliding the table 140 horizontally in and out the opening of the gantry 135. A controller 150 comprises all the components required to drive the gradient coils and the RF coil (for example, an RF transmitter, an output amplifier and the like), to acquire the response signals from the body-part under analysis (for example, an input amplifier, an Analog-To-Digital Converter (ADC) and the like) and to drive the motor of the base 145. An injector head assembly 155 is used to inject one or more medical fluids into the patient during his/her analysis.

The MRI system 100 comprises the following components in the equipment room 110. One or more cabinets 160 for the MRI scanner 135 house power components (for conditioning and distributing electrical power supply), gradient components (for sending electric current to the gradient coils), RF components (for sending electric pulses to the RF coil and receiving the response signals) and cooling components (such as a helium pump for circulating liquid helium around the superconducting magnet and a heat exchanger for cooling the gradient coils). A hydraulic controller (or drive) 165 is used to drive the injector head assembly 155 (with the injector head assembly 155 and the hydraulic drive 165 that together form a corresponding injector system). The cabinets 160 are connected to the MRI scanner 135 and the hydraulic controller 165 is connected to the injector head assembly 155 via corresponding cables (not shown in the figure) passing through the penetration panel 120.

The MRI system 100 comprises the following components in the control room 115. A computing machine, or simply a computer, 170 (for example, a Personal Computer, PC) is used to control the MRI scanner 135 and the injector head assembly 155 remotely; moreover, the computer 170 is used to manage the analyses being performed. The computer 170 is connected to the cabinets 160 and to the hydraulic controller 165 via corresponding cables, passing outside the scanner room 105 (not shown in the figure).

In operation, every time a (new) analysis of a body-part of a patient is to be performed, the following operations are carried out by a health care professional (or more). Particularly, the health care professional lets the patient lay down onto the table 140 (extracted from the gantry 135). Moreover, the health care professional sets up the injector head assembly 155 for the analysis and connects it to the patient. The health care professional then actuates the motor of the base 145 to cause the table 140 to slide into the gantry 135, until the body-part reaches a proper position within its opening. At this point, the health care professional leaves the scanner room 105. The health care professional then controls the analysis via the computer 170 from the control room 115. Particularly, the health care professional selects an injection program for the injector head assembly 155 and starts it. The health care professional may now actuate the gantry 135, so as to register corresponding images of the body-part that are saved and displayed. Once the analysis of the body-part has been completed, the health care professional enters the scanner room 105 and actuates the motor of the base 145 to cause the table 140 to slide out the opening of the gantry 135. The health care professional disconnects the injector head assembly 155 from the patient so that he/she may be let to get off the table 140.

Figure 2:
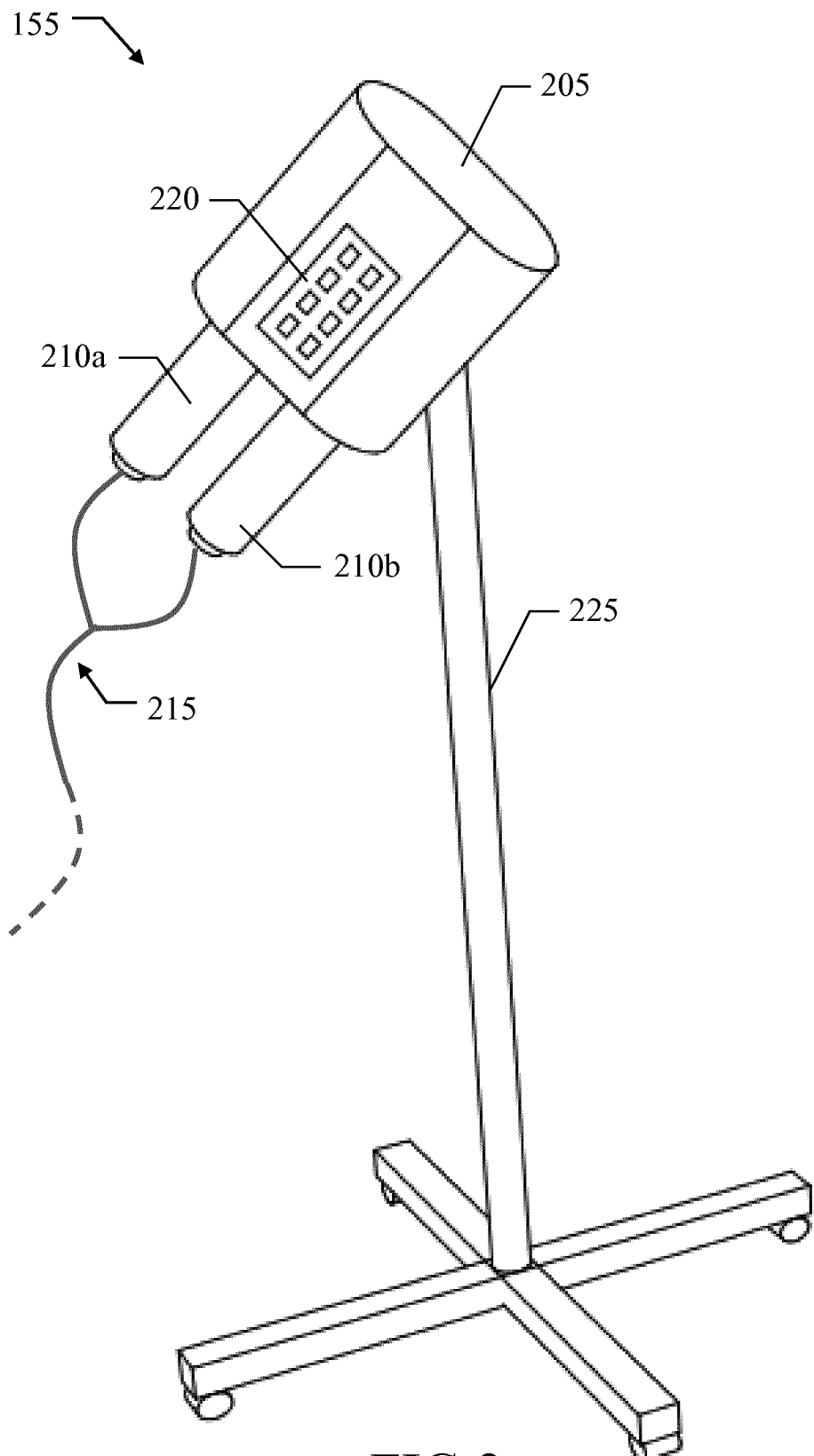
FIG. 2 shows a pictorial representation of an injector head assembly wherein the solution according to an embodiment of the present disclosure may be implemented.

With reference now to FIG. 2, a pictorial representation is shown of the injector head assembly 155 wherein the solution according to an embodiment of the present disclosure may be implemented.

The injector head assembly 155 comprises the following components. An injector head 205 is provided with two syringes 210a and 210b for loading and delivering corresponding medical fluids. For example, the medical fluids are a contrast agent (for example, a gadolinium complex for a standard MRI analysis or a paramagnetic lanthanide complex for an MRI-CEST analysis), alone or in combination with a saline to be delivered before (pre-flush), after (post-flush) or between (interphase) the delivery of the contrast agent, or in rapid alternate succession with the contrast agent. The injector head 205 controls corresponding plungers of the syringes 210a, 210b (not visible in the figure) to load and to deliver their medical fluids. A delivery set 215 is used to connect the syringes 210a, 210b to the patient. For example, the delivery set 215 comprises two (flexible) tubes that are connected to corresponding orifices of the syringes 210a, 210b; a Y-connector joins the tubes to another (flexible) tube, which ends with a connector for a peripheral catheter. The injector head 205 exposes a panel 220 (for example, a keypad with a series of membrane keys and a series of LEDs), which is used to interact with the injector head assembly 155. The injector head 205 is supported by a stand 225. The stand 225 is provided with wheels that facilitate moving the whole injector head assembly 155; moreover, the wheels have a foot brake to secure the injector head assembly 155 in position. Alternatively, the injector head 205 may be ceiling or wall mounted (not shown in the figures).

The injector head assembly 155 is resistant to magnetic fields and substantially MR conditional (to avoid, or at least largely attenuate, any known cause of interference with operation of the MRI system). For example, the injector head assembly 155 has no ferromagnetic material, has an enclosure that substantially shields emission of RF radiations, has filters that provide advanced decoupling at critical positions, is accurately calibrated (with a specific and limited allowed maximum tolerance) and is validated in the factory and in the field.

In operation, for every (new) analysis of a body-part of a patient the health care professional programs an injection profile (comprising one or more phases each one defined by flow rate, volume and time of the medical fluids to be injected) onto the computer (not shown in the figure), for example, by selecting it among pre-defined injection profiles for different types of analyses. The health care professional then loads the injector head with the required medical fluids. For this purpose, the health care professional tilts the injector head 205 to a load position (with the syringes 210a, 210b facing upwards, not shown in the figure) and enters a command onto the keypad 220 for causing the injector head 205 to advance the plungers of the syringes 210a, 210b until reaching a front end of their barrels. The health care professional connects the orifices of the syringes 210a, 210b to containers of the medical fluids (not show in the figure). The health care professional enters a command onto the keypad 220 for causing the injector head 205 to retract the plungers of the syringes 210a, 210b until the corresponding amounts of the medical fluids have been loaded (after that he/she disconnects the containers from the syringes 210a, 210b). The health care professional inserts the peripheral catheter into a peripheral vein of the patient and connects the delivery set 215 thereto. The health care professional tilts the injector head 205 to a run position (with the syringes 210a, 210b directed downwards, as shown in the figure) and enters a command onto the keypad 220 for causing the injector head 205 to advance the plungers of the syringes 210a, 210b for delivering the corresponding medical fluids according to the selected injection profile.

Figure 3:
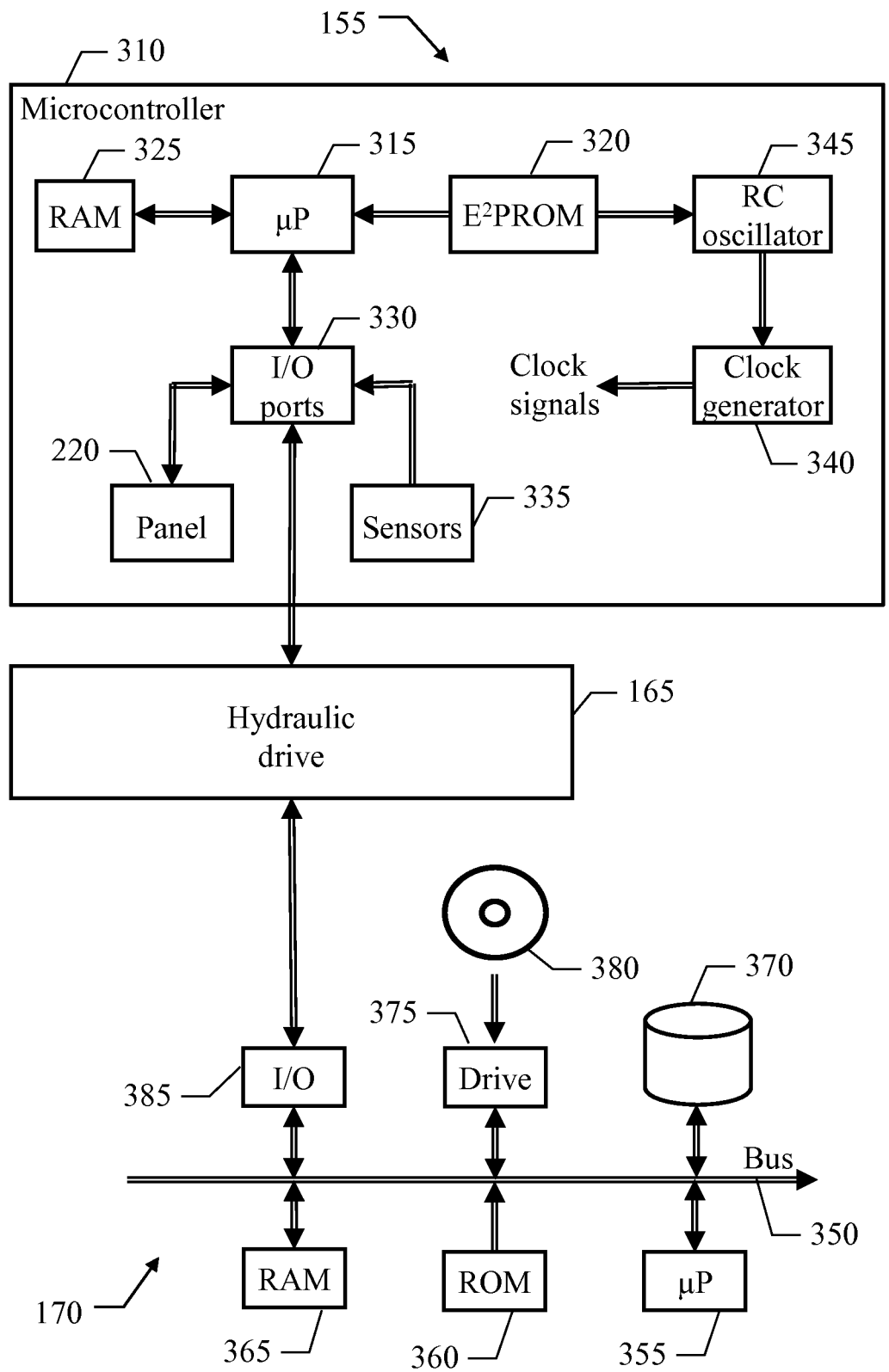
FIG. 3 shows the main hardware components that may be used to implement the solution according to an embodiment of the present disclosure.

With reference now to FIG. 3, the main hardware components are shown that may be used to implement the solution according to an embodiment of the present disclosure.

Starting from the injector head assembly 155, it embeds a microcontroller (or MicroController Unit, MCU) 310. A microprocessor (IP) 315 controls operation of the microcontroller 310. A non-volatile memory 320 (for example, a flash EPROM) stores a control program (firmware) of the microprocessor 315 and a volatile memory (RAM) 325 is used as a working memory by the microprocessor 315. Moreover, the microcontroller 310 comprises a number of Input/Output (I/O) ports 330. The I/O ports 330 are used to communicate with peripheral units of the injector head assembly 155 and with its hydraulic controller 165; particularly, the peripheral units of the injector head assembly 155 comprise the keypad and the LEDs of the panel 220 and one or more sensors 335 (for example, pressure sensors for the syringes, tilt sensors for the injector head). A clock generator 340 generates one or more clock signals (with corresponding clock frequencies). The clock signals are timing signals that oscillate between two different states (for example, square waves with a 50% duty cycle); the clock signals are used to synchronize operation of the microcontroller 310. For example, the clock signals comprise a system clock signal for the microprocessor 315 and one or more I/O clock signals for the I/O ports 330. The clock generator 340 exploits a Resistor/Capacitor (RC) oscillator 345 (with low RF emissions). The RC oscillator provides a reference clock signal, which is used to generate all the clock signals. The reference clock signal has a reference clock frequency defined by a corresponding RC network, with the reference clock frequency that may be adjusted by updating the RC network (for example, the capacitance of one or more variable capacitors thereof).

Passing to the computer 170, it comprises several units that are connected among them through a bus structure 350 (with one or more levels). Particularly, one or more microprocessors (μP) 355 control operation of the computer 170; a non-volatile memory (ROM) 360 stores basic code for a bootstrap of the computer 170 and a volatile memory (RAM) 365 is used as a working memory by the microprocessors 355. The computer 170 is provided with a mass-memory for storing programs and data; particularly, the mass memory comprises one or more hard disks 370 and a drive 375 for reading/writing optical disks 380 (for example, CDs or DVDs). Moreover, the computer 170 comprises a number of controllers for peripheral (I/O) units 385; for example, the peripheral units 385 comprise a keyboard, a mouse, a monitor, a network adapter (NIC) for connecting to the cabinets of the MRI system, to the hydraulic controller 165 of the injector head assembly 155 and to a communication network, such as the Internet (not shown in the figure).

In the solution according to an embodiment of the present disclosure (as described in detail in the following), any clock frequency may be adjusted (from a current value to a new value thereof) in an operative condition of the MRI system, i.e., when the MRI system is in the field (for example, in its MRI installation), ready to be used by health care professionals to analyze body-parts of patients (and then without requiring any dedicated equipment that may instead be available in the factory). For this purpose, a memory structure is provided in the MRI system storing an indication of a plurality of candidate values of the clock frequency (for example, a list/range thereof). In response to a manual command and/or to a detection of a degradation of the images, the new value is selected from the candidate values.

This solution originates from the intuition that harmonics of the corresponding clock signal may interfere with an operating frequency of the MRI scanner, and particularly with the operating frequency of its RF coil (generally of the order of some MHz, varying with the stationary magnetic field generated by its superconducting magnet). More specifically, when any harmonic of the clock signal and the operative frequency of the MRI scanner are close together, the left over RF emissions of the injector head assembly (after their shielding) may adversely affect operation of the MRI scanner in combination with certain circumstances (for example, component drifts, position of the injector head assembly, room temperature).

The proposed solution allows removing, or at least largely attenuating, any degradation of the images generated by the MRI system that may be caused by the clock signals; as a result, the images are free, or at least far less affected, by artefacts that might blemish them.

In this way, it is possible to intervene promptly (either manually or automatically) in whatever situation. Particularly, it is possible to intervene on-site as soon as the artefacts appear even if this occurs after a relatively long lifetime of the injector head assembly, sporadically, under different operative conditions of the MRI system, with different MRI systems. Indeed, the proposed solution is of instant application (without requiring any investigation for identifying the actual contingent cause of the artefacts and the candidate values of the clock frequencies that should remove the artefacts) and independent of the MRI system wherein the injector system is used.

All of the above improves a quality of the images and an accuracy of the analyses of the corresponding body-parts (and then of the diagnosis/therapy of possible lesions thereof). Moreover, this has a beneficial effect on a corresponding customer satisfaction.

Figure 4:
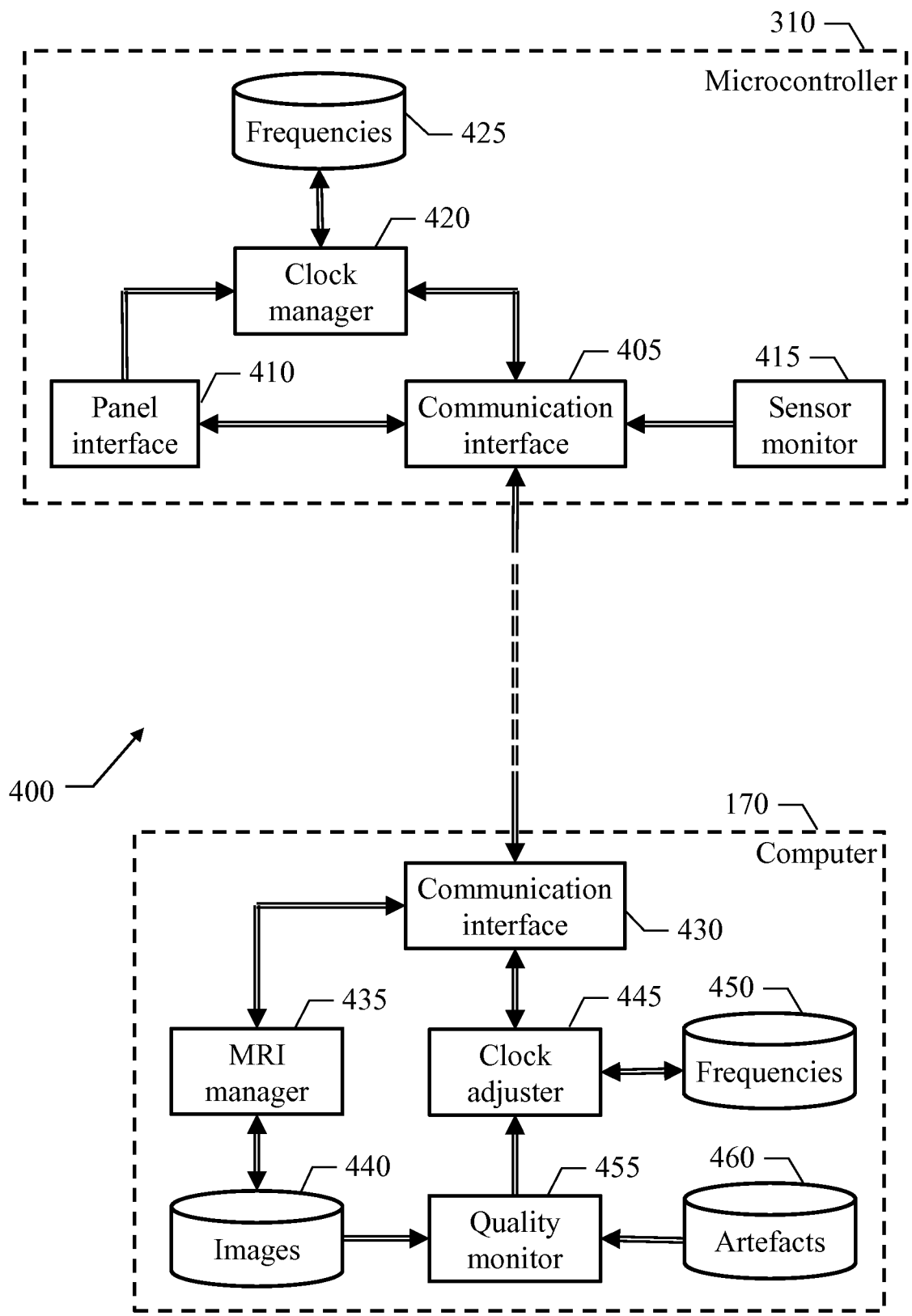
FIG. 4 shows the main program components that may be used to implement the solution according to an embodiment of the present disclosure.

With reference now to FIG. 4, the main program components are shown that may be used to implement the solution according to an embodiment of the present disclosure.

Particularly, all the programs components (executables and data) are denoted as a whole with the reference 400. In this respect, each executable may be a module, segment or portion of code, which comprises one or more instructions for implementing the specified logical function.

Starting from the microcontroller 310 of the injector head assembly, its program components implement a (low-level) firmware that controls the hardware components of the microcontroller 310. The firmware is stored in the non-volatile memory and loaded (at least partially) into the working memory of the microcontroller 310 when its executables are running. The firmware is pre-installed into the non-volatile memory, for example, from an external computer (not shown in the figure). Particularly, the firmware of the microcontroller 310 comprises the following program components.

A (microcontroller) communication interface 405 is used to communicate with the computer 170 (via the hydraulic controller, not shown in the figure). A panel interface 410 controls the panel of the injector head; particularly, the panel interface 410 receives commands entered with the keypad and drives the LEDs of the panel. A sensor monitor 415 collects corresponding measurements provided by the sensors of the injector head (for example, with a polling technique). Both the panel interface 410 and the sensor monitor 415 interact with the communication interface 405 (to send commands entered with the keypad and the measurements provided by the sensors to the hydraulic controller and to receive commands for the LEDs from the hydraulic controller). A clock manager 420 controls the clock signals of the microcontroller 310. Particularly, the clock manager 420 sets the reference clock frequency and generates all the clock signals accordingly. Moreover, in the solution according to an embodiment of the present disclosure, the clock manager 420 further adjusts the reference clock frequency (in response to a manual command and/or to a detection of a degradation of the images). For this purpose, the clock manager 420 accesses (in read/write mode) a file storing corresponding (local) frequency information 425. The frequency information 425 comprises a current value of the reference clock frequency (for example, stored in a pre-defined location of the non-volatile memory); the reference clock frequency is pre-set (in the factory) to a nominal value (for example, 7.96 MHz in nominal conditions with a power supply of 5V and a room temperature of 25° C.). Moreover, in the solution according to an embodiment of the present disclosure, the frequency information 425 comprises information for adjusting the reference clock frequency, and particularly an indication of two or more candidate values for the clock frequency. In a possible implementation, the frequency information 425 comprises a candidate list of the candidate values of the reference clock frequency (comprising its nominal value), with the current value of the reference clock frequency that may be selected within it. In another implementation, the frequency information 425 comprises a candidate range of the candidate values of the reference clock frequency (comprising its nominal value), with the current value of the reference clock frequency that may be selected within it. The implementation based on the candidate list is simpler, whereas the implementation based on the candidate range is more flexible. The clock manager 420 interacts with the panel interface 410 (when the reference clock frequency may be adjusted locally) and/or with the communication interface 405 (when the reference clock frequency may be adjusted remotely from the computer 170).

In any case, an allowable range of the reference clock frequency (defined by the low end and the high end of the candidate list or directly by the candidate range) is relatively small. For example, the reference clock frequency has a (nominal) tolerance around its nominal value, which defines a corresponding nominal range ensuring the correct operation of the microcontroller 310 (for example, ±2-4%); nevertheless, the RC oscillator is calibrated (in the factory) more precisely, so that the reference clock frequency has an (actual) tolerance around its nominal value lower than the nominal tolerance (for example, equal to 10-25%, preferably equal to 12-20% and still more preferably equal to 14-18%, such as equal to 16% of the nominal tolerance, like ±0.4-0.6%). In this case, the allowable range is defined around the nominal value according to a pre-defined percentage (such as 50-70%) of a difference between the nominal tolerance and the actual tolerance; for example, with the nominal value of 7.9600 MHz and the nominal tolerance of ±3%, if the actual tolerance is ±0.5% the allowable range may be 7.96±(3−0.5)·0.5%≈7.96±0.01=7.86−8.06 MHz. In this way, the (adjusted) reference clock frequency always remains within the nominal range.

Moreover, it is also possible to validate the candidate values (in the factory and/or in the field) by measuring an operative parameter of the microcontroller 310 and verifying whether the operative parameter is within allowable limits (ensuring correct operation of the microcontroller 310). For example, the operative parameter is a baud rate of the I/O port used to communicate with the hydraulic controller (which baud rate also provides an indirect measurement of the reference clock frequency, since the latter is equal to the baud rate multiplied by a known scaling factor). The baud rate (average number of symbols per second) may be determined by measuring (for example, with an oscilloscope) the time required to transfer one symbol, with this measurement that is repeated several times to compensate for different delay times of rising and falling edges of the symbols.

Passing to the computer 170, its program components implement a (high-level) software that implements the functionalities of the computer 170 (together with an operating system and other application programs, not shown in the figure). The software is stored in the mass memory and loaded (at least partially) into the working memory of the computer 170 when its executables are running. The software is initially installed into the mass memory, for example, from removable storage units or from the communication network. Particularly, the software of the computer 170 comprises the following program components.

A (computer) communication interface 430 is used to communicate with the microcontroller 310 (via its hydraulic controller) and with the MRI scanner, not shown in the figure (via its cabinets). An MRI manager 435 is used to control the MRI scanner 135 and the injector head assembly 155 remotely; for example, the MRI manager 435 allows operating the MRI scanner (i.e., its motor and gantry) and the injector head, and it allows monitoring them. Moreover, for each analysis that is in progress, the MRI manager 435 receives response signals representing the response of corresponding locations of the body-part to the magnetic field applied thereto, and it generates one or more images representing the body-part (with each image defined by a matrix of cells containing the values of voxels defining their brightness as a function of the response of the corresponding locations of the body-part). The MRI manager 435 allows displaying, archiving and exporting the images. For this purpose, the MRI manager 435 controls (in read/write mode) a repository 440 storing the images, at least for the analysis that is in progress. In the solution according to an embodiment of the present disclosure, a clock adjuster 445 is used to adjust the reference clock frequency of the microcontroller 310 remotely (manually and/or automatically). For this purpose, the clock adjuster 445 interacts with the communication interface 430. Moreover, the clock adjuster 445 controls (in read/write mode) a file mirroring the frequency information 425, denoted as (remote) frequency information 450. A quality monitor 455 may also be provided for monitoring a quality of the images and adjusting the reference clock frequency accordingly. The quality monitor 455 accesses (in read mode) the repository of the images 440 and it interacts with the clock adjuster 445. Moreover, the quality monitor 455 accesses (in read mode) a repository of (known) artefacts 460. For example, the artefacts 460 are defined by corresponding patterns, which may have been pre-determined with cognitive techniques (and particularly machine learning techniques) from (sample) images identified to contain artefacts; the sample images may have been collected manually in the factory, downloaded from working MRI systems (such as images recognized manually by health care professionals or automatically when preceding a manual change of the reference clock frequency).

Figure 5A:
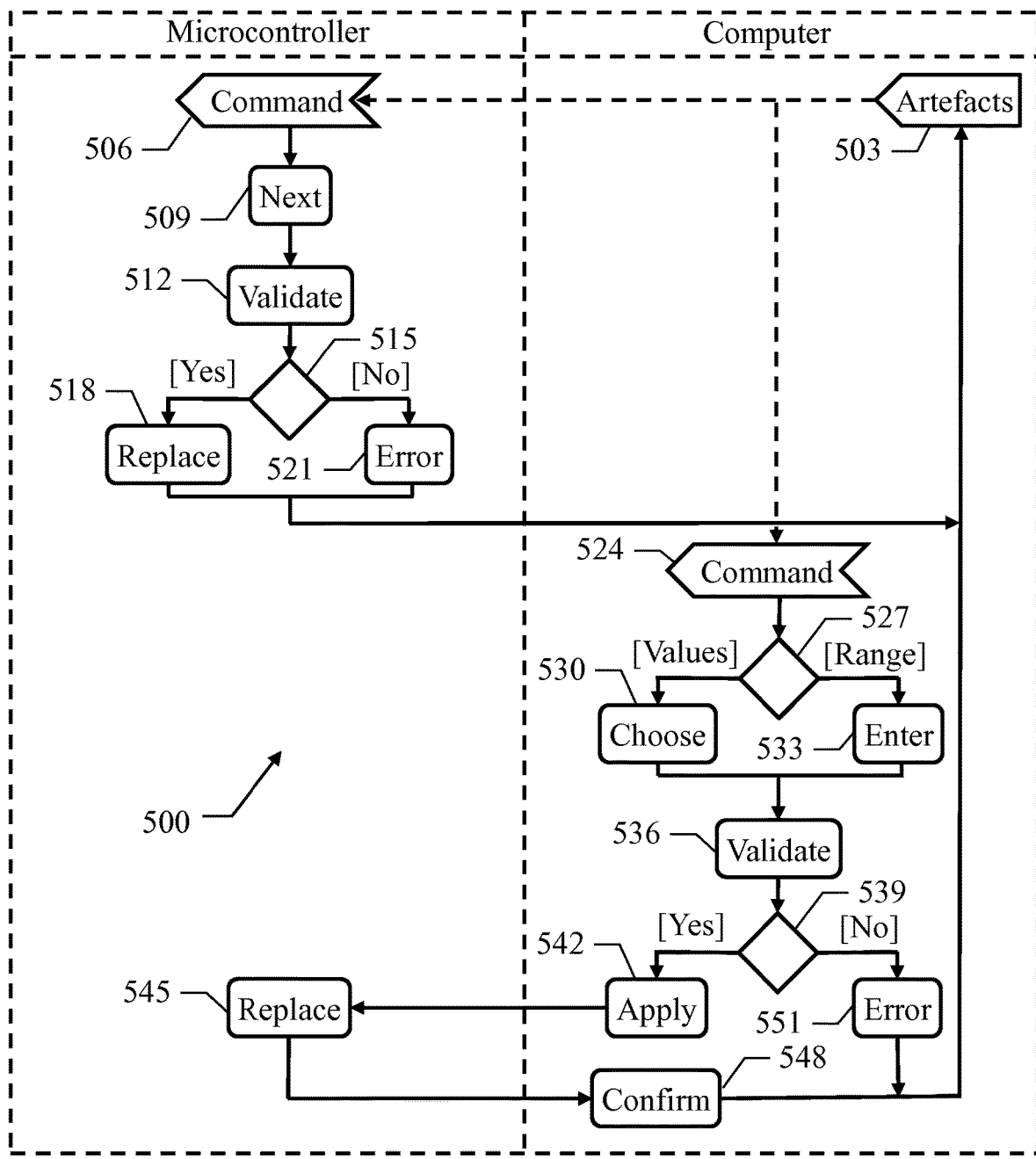
FIG. 5A-FIG. 5B show an activity diagram describing the flow of activities relating to an implementation of the solution according to an embodiment of the present disclosure.
Figure 5B:
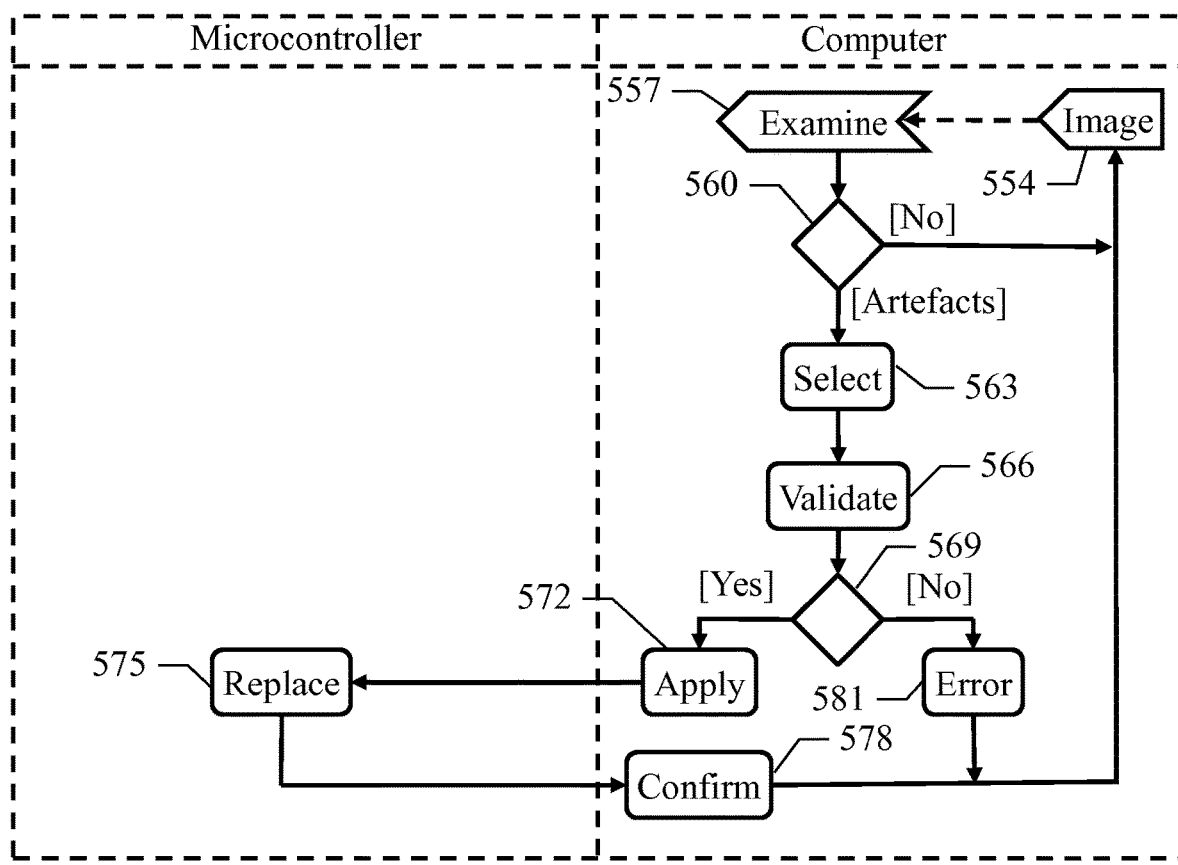

With reference now to FIG. 5A-FIG. 5B, an activity diagram is shown describing the flow of activities relating to an implementation of the solution according to an embodiment of the present disclosure.

Particularly, the diagram represents an exemplary process that may be used to operate the MRI system (and particularly its injector head assembly) as a whole with a method 500. In this respect, each block may correspond to one or more executable instructions for implementing the specified logical function on the computer of the MRI system or on the microcontroller of the injector head assembly.

Starting from block 503 in the swim-lane of the computer, a generic health care professional may detect any (significant) artefacts in the images; for example, this happens when the images displayed onto the monitor (for an analysis that is in progress) are blemished by lines crossing them and/or some portions of the corresponding body-part fade (down to disappear).

In an embodiment of the present disclosure, when this happens the health care professional (typically a radiographer) may ask another health care professional (typically a nurse) to change the reference clock frequency on the injector head assembly. For example, the panel interface may be programmed to recognize a pre-defined key combination of the panel for this purpose (for example, two or more keys pressed together). In this way, the possibility of changing the reference clock frequency is added without requiring any modification of the physical structure of the injector head assembly; moreover, the key combination avoids, or at least substantially reduces, any risk of changing the reference clock frequency accidentally. Particularly, moving to the swim-lane of the microcontroller, the nurse enters this key combination at block 506. In response thereto, assuming that the local frequency information stored in the corresponding file comprises the candidate list (for the candidate values of the reference clock frequency), the clock manager at block 509 determines the new value of the reference clock frequency by moving to a next candidate value that follows the current value in a wrap-around way (i.e., simply toggling to the other one when only two candidate values are available). The clock manager at block 512 validates the new value of the reference clock frequency (set thereto provisionally). For example, the clock manager (via the microcontroller communication interface) sends a validation command to the hydraulic controller, which validation command causes the hydraulic controller to measure the baud rate of the corresponding I/O port as above (by using its very accurate quartz oscillator) and to return the measured value to the clock generator. The flow of activity branches at block 515 according to a result of this operation. If the baud rate is within its allowable limits, the clock manager at block 518 replaces the current value of the reference clock frequency (in the file of the local frequency information) with its new value and it causes the panel interface to provide a special flickering of the LEDs of the panel (as a feedback to the nurse of the successfully change of the reference clock frequency); at the same time, if the MRI system also supports the possibility of changing the reference clock frequency remotely from its computer, the clock manager sends a corresponding notification (comprising the new value of the reference clock signal) to the clock adjuster of the computer (via the microcontroller communication interface), so as to cause it to update the remote frequency information accordingly in the corresponding file. Conversely, if the baud rate is not within the allowable limits, the clock generator at block 521 notifies an error condition to the nurse, for example, by causing the panel interface to switch-on a corresponding LED of the panel. In both cases, the process returns to the block 503. Particularly, when the block 503 is reached from the block 518 the radiographer may now verify whether the artefacts have actually disappeared from the images; conversely, when the block 503 is reached from the block 521 the operation of the injector head assembly remains unchanged and the nurse may try a further candidate value of the reference clock frequency (if available) or he/she may contact a corresponding technical support.

In addition or in alternative, when the health care professional detects any (significant) artefacts in the images at block 503, he/she may change the reference clock frequency directly on the computer; for example, the MRI manager may expose a command (for example, a menu option) to invoke this function, which command is available only when the MRI manager has been accessed with a user account (protected by a corresponding password) having corresponding authorizations. In this way, the possibility of changing the reference clock frequency is added without requiring any modification of the injector head assembly. Particularly, the health care professional enters this command at block 524. The flow of activity branches at block 527 according to the type of the frequency information. Particularly, when the remote frequency information comprises the candidate list (of the candidate values of the reference clock frequency), the clock adjuster at block 530 prompts the health care professional to choose a new value of the reference clock frequency among the candidate values different from the current value (with this operation that is performed automatically when only two candidate values are available). Conversely, when the remote frequency information comprises the candidate range (of the candidate values of the reference clock frequency), the clock adjuster at block 533 prompts the health care professional to enter a new value of the reference clock frequency within the candidate range (for example, by typing it or by moving a corresponding slider). In both cases, the clock adjuster at block 536 validates the new value of the reference clock frequency (set thereto provisionally). For example, the clock adjuster (via the computer communication interface) sends a validation command to the hydraulic controller, which validation command causes the hydraulic controller to measure the baud rate of the corresponding I/O port as above and to return the measured value to the clock adjuster. The flow of activity branches at block 539 according to a result of this operation. If the baud rate is within the allowable limits, the clock adjuster at block 542 sends a command to the injector head assembly (via the computer communication interface) for changing the reference clock frequency to the new value. Moving to the swim-lane of the microcontroller, in response thereto the clock manager at block 545 replaces the current value of the reference clock frequency (in the file of the local frequency information) with its new value received from the computer and it returns a confirmation message thereto. Going back to the swim-lane of the computer, as soon as the clock adjuster receives this confirmation message at block 548, it displays a corresponding notification of the successfully change of the reference clock frequency; at the same time, the clock adjuster updates the remote frequency information accordingly in the corresponding file. Referring back to the block 539, if the baud rate is not within the allowable limits, the clock adjuster at block 551 displays a notification of a corresponding error condition. In both cases, the process returns to the block 503 from either the block 548 or the block 551. Particularly, when the block 503 is reached from the block 548 the health care professional may now verify whether the artefacts have actually disappeared from the images as above; conversely, when the block 503 is reached from the block 551 the operation of the injector head assembly remains unchanged and the health care professional may perform further attempts to change the reference clock frequency (if available) or he/she may contact the corresponding technical support as above.

In addition or in alternative, a loop is performed continually for triggering the change of the reference clock frequency automatically. The loop begins at block 554 whenever the MRI manager adds a (new) image to the corresponding repository. In response thereto, the quality monitor at block 557 examines this image to verify whether it contains any (known) artefacts; for example, the quality monitor applies cognitive techniques (and particularly object-detection techniques) to detect possible artefacts (as defined in the corresponding repository) in the image. The flow of activity branches at block 560 according to a result of this operation. If one or more artefacts have been detected in the image with an acceptable degree of confidence (for example, higher than a pre-defined threshold such as 50-70%), the clock adjuster at block 563 selects a new value of the reference clock frequency; for example, the new value is selected (to be different from the current value) in (pseudo-)random way within the candidate list or the candidate range (of the candidate values of the clock frequency). The clock adjuster at block 566 validates the new value of the reference clock frequency as above. In this case as well, the flow of activity branches at block 569 according to a result of this operation. If the baud rate is within the allowable limits, the clock adjuster at block 572 sends a command to the injector head assembly (via the computer communication interface) for changing the reference clock frequency to the new value. Moving to the swim-lane of the microcontroller, in response thereto the clock manager at block 575 replaces the current value of the reference clock frequency (in the file of the local frequency information) with its new value received from the computer and it returns a confirmation message thereto. Going back to the swim-lane of the computer, as soon as the clock adjuster receives this confirmation message at block 578, it displays a corresponding notification of the successfully change of the reference clock frequency (for example, in a pop-up window) and updates the remote frequency information accordingly in the corresponding file. Referring back to the block 569, if the baud rate is not within the allowable limits, the clock adjuster at block 581 displays a notification of a corresponding error condition (for example, again in a pop-up window); in this way, the health care professional is informed of the failed attempt to change the reference clock frequency and he/she may act accordingly (for example, by performing one or more attempts to change the reference clock frequency manually as described above). In both cases, the process returns to the block 554 from either the block 578 or the block 581 waiting for a next image.

Naturally, in order to satisfy local and specific requirements, a person skilled in the art may apply many logical and/or physical modifications and alterations to the present disclosure. More specifically, although this disclosure has been described with a certain degree of particularity with reference to one or more embodiments thereof, it should be understood that various omissions, substitutions and changes in the form and details as well as other embodiments are possible. Particularly, different embodiments of the present disclosure may even be practiced without the specific details (such as the numerical values) set forth in the preceding description to provide a more thorough understanding thereof; conversely, well-known features may have been omitted or simplified in order not to obscure the description with unnecessary particulars. Moreover, it is expressly intended that specific elements and/or method steps described in connection with any embodiment of the present disclosure may be incorporated in any other embodiment as a matter of general design choice. In any case, each numerical value should be read as modified by the term about (unless already done) and each range of numerical values should be intended as expressly specifying any possible number along the continuum within the range (comprising its end points). Moreover, ordinal or other qualifiers are merely used as labels to distinguish elements with the same name but do not by themselves connote any priority, precedence or order. The terms include, comprise, have, contain and involve (and any forms thereof) should be intended with an open, non-exhaustive meaning (i.e., not limited to the recited items), the terms based on, dependent on, according to, function of (and any forms thereof) should be intended as a non-exclusive relationship (i.e., with possible further variables involved), the term a/an should be intended as one or more items (unless expressly indicated otherwise), and the term means for (or any means-plus-function formulation) should be intended as any structure adapted or configured for carrying out the relevant function.

For example, an embodiment provides an MRI system. However, the MRI system may be of any type (for example, standard, of CEST type and so on).

In an embodiment, the MRI system is for generating one or more images of a body-part of a patient under analysis. However, the images may be in any number (for each analysis) and of any type (for example, in grey scale, colored and so on); moreover, the MRI system may be used to analyze any body-part (for example, organ, tissue) of any patient (for example, human or animal). In general, the MRI system may be operated by any qualified person (for example, any health care professional like a physician, a radiographer, a radiologist, a nurse or any combination thereof) for any purposes (for example, discovering new lesions, monitoring known lesions and so on).

In an embodiment, the MRI system comprises an injector head assembly for injecting at least one medical fluid into the patient. However, the injector head assembly may be of any type (for example, with one or more syringes, syringe-less and so on); moreover, the injector head assembly may be used to inject any number and type of medical fluids (for example, same or different contrast agents, alone or in combination with a saline).

In an embodiment, the injector head assembly comprises a control unit for controlling operation of the injector head. However, the control unit may be of any type (for example, a microcontroller, a PLC and so on).

In an embodiment, the injector head assembly comprises a clock unit for providing a clock signal with a clock frequency to the control unit. However, the clock unit may be of any type (for example, based on an RC oscillator, a quartz oscillator an so on, either internal or external to the control unit); moreover, the clock unit may provide any number and type of clock signals (for example, one or more clock signals generated from the reference clock signal, such as system clock, I/O clock(s), only the reference clock signal directly and so on).

In an embodiment, the MRI system comprises a memory structure storing an indication of a plurality of candidate values of the clock frequency. However, the memory structure may be of any type (for example, a file, a table, a database and the like provided in the injector head assembly, in its driving device, in the computing machine or any combination thereof); moreover, the memory structure may store any indication of the candidate values (for example, a list of values, a range of values, a rule for calculating the values and so on).

In an embodiment, the MRI system comprises means for adjusting the clock frequency (in an operative condition of the MRI system) from a current value to a new value. However, the means for adjusting may be implemented with any structure (for example, responsive to a manual command, to a degradation of the images or to both of them) and in any position (for example, in the injector head assembly, in the computer controlling the MRI system, in a dedicated device or any combination thereof); moreover, the current/new values may be of any type.

In an embodiment, the MRI system comprises means for selecting the new value among the candidate values. However, the new value may be selected in any way (for example, manually, completely automatically, automatically but requiring a manual confirmation, in either a random or deterministic way, such as according to a wrap-around succession with any pitch, to any formula, and so on) in whatever scenario (i.e., manual/automatic, implemented in any position and so on).

In an embodiment, the means for adjusting comprise means for entering an adjusting command manually. However, the manual command may be entered in any way (for example, with physical or virtual elements, like keys, menu options, and so on, either available only to authorized persons or to everybody) and in any position (see above) by any qualified person (for example, health care professional, technical staff).

In an embodiment, the means for adjusting comprise means for triggering the adjusting of the clock frequency in response to the adjusting command. However, the adjustment of the clock frequency may be triggered in any way (for example, directly, requiring a further confirmation and so on).

In an embodiment, the means for adjusting comprise means for monitoring the images generated by the MRI system. However, the images may be monitored in any way (for example, always, periodically, random, upon request and so on) and in any position (see above).

In an embodiment, the means for adjusting comprise means for detecting the degradation of the images according to artefacts thereof. However, the degradation of the images may be detected in any way (for example, with cognitive, fuzzy-logic, artificial-intelligence techniques and so on, either locally or remotely such as exploiting a corresponding service offered over the communication network) and in any position (see above) according to any artefacts (for example, lines, spots, holes and so on).

In an embodiment, the means for adjusting comprise further means for triggering the adjusting of the clock frequency in response to the degradation of the images. However, the adjustment of the clock frequency may be triggered in any way (for example, automatically, requiring a manual confirmation and so on).

In an embodiment, the injector head assembly comprises the means for adjusting. However, the means for adjusting may be implemented with any structure in the injector head assembly (for example, in its control unit, with a dedicated unit and so on).

In an embodiment, the injector head assembly comprises a keypad having a plurality of keys for entering commands for controlling operation of the injector head assembly. However, the keys may be in any number and of any type (for example, membrane keys, virtual keys of a touch-screen and so on); moreover, these keys may be provided for entering any number and type of commands (for example, load, start, stop, pause and so on).

In an embodiment, the means for entering the adjusting command are comprised in the keypad. However, the adjusting command may be entered with the keypad in any way (for example, via a combination of elements provided for other purposes, with a dedicated element or any combination thereof).

In an embodiment, the adjusting command consists of a pre-defined combination of the keys of the keypad. However, the key combination may be of any type (for example, two or more keys to be pressed at the same time, two or more keys to be pressed in short sequence and so on).

In an embodiment, the MRI system comprises a computing machine for controlling operation of the MRI system. However, the computing machine may be of any type (for example, a computer, a tablet, a dedicated device and so on); moreover, the computing machine may be used to control operation of the MRI system in any way (for example, for performing partial, different and/or additional operations with respect to the ones mentioned above).

In an embodiment, the computing machine comprises the means for adjusting. However, the means for adjusting may be implemented with any structure in the computing machine (for example, with a plug-in, a dedicated program and so on).

In an embodiment, the MRI system comprises means for measuring at least one operative parameter of the injector system. However, the means for measuring may be implemented with any structure (for example, in the hydraulic controller or any other driving device of the injector head assembly, in the injector head assembly, in a dedicated device and so on); moreover, any number and type of operative parameters (for example, relating to communication ports, I/O units and so on) may be measured in any way (for example, during normal operation of the injector system or after stopping its operation).

In an embodiment, the MRI system comprises means for validating the new value according to said at least one operative parameter. However, the means for validating may be implemented with any structure (for example, in the computing machine, in the driving device of the injector head assembly, in the injector head assembly and so); moreover, the new value may be validated in any way (for example, one-shot, continually and so on). In any case, this feature may also be omitted in any of the above-described embodiments of the present disclosure, up to all of them.

In an embodiment, said at least one operative parameter comprises a frequency of a communication port of the injector head assembly. However, the communication port may be of any type (for example, serial, parallel and so on) for coupling the injector head assembly with any other device (for example, its driving device, the computing machine and so on).

In an embodiment, the MRI system comprises a driving device for driving the injector head assembly. However, the driving device may be of any type (for example, hydraulic, electric and so on).

In an embodiment, the means for measuring are comprised in the driving device. However, the means for measuring may be implemented with any structure in the driving device (for example, in a control unit thereof, in a dedicated unit and so on).

In an embodiment, the memory structure stores a candidate list of the candidate values of the clock frequency. However, the candidate list may be of any type (for example, listing the candidate values, negative and/or positive offsets from a nominal value and so on).

In an embodiment, the memory structure stores a candidate range of the clock frequency. However, the candidate range may be of any type (for example, extending around the nominal value in both directions, only below, only above).

In an embodiment, the clock frequency has a nominal value with a nominal tolerance. However, the nominal value and the nominal tolerance may be of any amount (for example, with the nominal tolerance that is bilateral, unilateral and so on).

In an embodiment, the candidate values are comprised in a nominal range defined by the nominal value and the nominal tolerance. However, the allowable range corresponding to the candidate values may be defined in any way according to the nominal range (for example, around the nominal value according to any percentage of the nominal tolerance, of a difference between the nominal tolerance and an actual tolerance, up to be equal to the nominal range). In any case, the possibility is not excluded of defining the candidate values in any different way (even independently of the nominal range).

In an embodiment, the MRI system comprises means for generating magnetic pulses at a radio frequency. However, the means for generating the magnetic pulses may be implemented with any structure (for example, varying according to the corresponding body-part to be analyzed or universal) for providing any type of pulses with any radio frequency (either fixed or variable).

In an embodiment, the new value has no harmonic frequencies matching the radio frequency. However, the new value may be pre-determined to avoid any match with any number and type of harmonics (down to the fundamental frequency only) of the radio frequency (for example, differing from the radio frequency by more than a minimum value, down to zero). In any case, the possibility is not excluded of determining the new value freely and then simply validating it.

In an embodiment, the clock unit comprises an RC oscillator for generating the clock signal. However, the RC oscillator may be of any type (for example, with any number and type of resistors and capacitors, and so on).

In an embodiment, the means for adjusting comprises means for setting the RC oscillator according to the new value of the clock signal. However, the means for setting may be implemented with any structure (for example, based on variable resistors and/or capacitors and so on).

An embodiment provides an injector system for use in the above-described MRI system (with the injector system that comprises said injector head assembly, which in turn comprises said memory structure, said means for adjusting and said means for selecting). However, the injector system may be of any type (for example, the injector head assembly with its driving device or the injector head assembly alone, both of them with any number of possible additional components like a remote control and so on); moreover, the injector system may be put on the market as a stand-alone product for use with any MRI system, even of standard type.

An embodiment provides a computing machine for controlling operation of the above-described MRI system, which computing machine comprises said memory structure, said means for adjusting and said means for selecting. However, the computing machine may be of any type (see above).

Generally, similar considerations apply if the MRI system, the injector system and the computing machine each one has a different structure or comprises equivalent components (for example, of different materials) or it has other operative characteristics. In any case, every component thereof may be separated into more elements, or two or more components may be combined together into a single element; moreover, each component may be replicated to support the execution of the corresponding operations in parallel. Moreover, unless specified otherwise, any interaction between different components generally does not need to be continuous, and it may be either direct or indirect through one or more intermediaries.

An embodiment provides a method for managing an injector head assembly (adapted to inject at least one medical fluid into a patient under analysis in an MRI system adapted to generate one or more images of a body-part of the patient). The injector head assembly comprises a control unit for controlling operation of the injector head assembly. The injector head assembly comprises a clock unit for providing a clock signal with a clock frequency to the control unit. The method is characterized by adjusting the clock frequency in an operative condition of the MRI system from a current value to a new value, and selecting the new value among a plurality of candidate values of the clock frequency from an indication thereof stored in a memory structure of the MRI system. Said step of adjusting the clock frequency comprises entering an adjusting command manually and triggering the adjusting of the clock frequency in response to the adjusting command; in addition or in alternative, said step of adjusting the clock frequency comprises monitoring the images generated by the MRI system, detecting a degradation of the images according to artefacts thereof and triggering the adjusting of the clock frequency in response to the degradation of the images.

The method further comprises steps for implementing the above-mentioned functions. The considerations pointed out above for the MRI system and the injector head assembly apply mutatis mutandi to the corresponding steps of the method.

More generally, similar considerations apply if the same solution is implemented with an equivalent method (by using similar steps with the same functions of more steps or portions thereof, removing some non-essential steps or adding further optional steps); moreover, the steps may be performed in a different order, concurrently or in an interleaved way (at least in part).

An embodiment provides a computer program configured for causing a computing system to perform the method described above when the computer program is executed on the computing system.

An embodiment provides a computer program product that comprises a computer readable storage medium embodying a computer program, the computer program being loadable into a working memory of a computing system thereby configuring the computing system to perform the same method.

However, the computer program may be implemented as a stand-alone module, as a plug-in for a pre-existing computer program (for example, the clock manager in the microcontroller of the injector head assembly or the MRI manager in the computing machine of the MRI system), or even directly in the latter. The computer program may be executed on any computing system (for example, the microcontroller of the injector head assembly, the computing machine of the MRI system, the driving device of the injector head assembly, a dedicated device, either standalone or with distributed structure based on any architecture, such as local, wide area, global, cellular or satellite network, and exploiting any type of wired and/or wireless connections). In any case, similar considerations apply if the computer program is structured in a different way, or if additional modules or functions are provided; likewise, the memory structures may be of other types, or may be replaced with equivalent entities (not necessarily consisting of physical storage media). The computer program may take any form suitable to be used by any computing system (see above), thereby configuring the computing system to perform the desired operations; particularly, the computer program may be in the form of external or resident software, firmware, or microcode (either in object code or in source code for example, to be compiled or interpreted). Moreover, it is possible to provide the computer program on any computer readable storage medium. The storage medium is any tangible medium (different from transitory signals per se) that may retain and store instructions for use by the computing system. For example, the storage medium may be of the electronic, magnetic, optical, electromagnetic, infrared, or semiconductor type; examples of such storage medium are fixed disks (where the computer program may be pre-loaded), removable disks, memory keys (for example, USB), and the like. The computer program may be downloaded to the computing system from the storage medium or via a network (for example, the Internet, a wide area network and/or a local area network comprising transmission cables, optical fibers, wireless connections, network devices); one or more network adapters in the computing system receive the computer program from the network and forwards it for storage in one or more storage devices of the computing system. In any case, the solution according to an embodiment of the present disclosure lends itself to be implemented even with a hardware structure (for example, by electronic circuits integrated in one or more chips of semiconductor material), or with a combination of software and hardware suitably programmed or otherwise configured.

The invention claimed is:

1. An MRI system for generating one or more images of a body-part of a patient under analysis, wherein the MRI system comprises:
   an injector head assembly configured for injecting at least one medical fluid into the patient, the injector head assembly including a control unit configured for controlling operation of the injector head assembly and a clock unit configured for providing a clock signal with a clock frequency to the control unit;
   wherein the MRI system includes a memory structure storing an indication of a plurality of candidate values of the clock frequency, means for adjusting the clock frequency in an operative condition of the MRI system from a current value to a new value, and means for selecting the new value among the candidate values; and wherein the means for adjusting include means for entering an adjusting command manually and means for triggering the adjusting of the clock frequency in response to the adjusting command; and/or means for monitoring the images generated by the MRI system, means for detecting a degradation of the images according to artifacts of the images, and further means for triggering the adjusting of the clock frequency in response to the degradation of the images.

2. The MRI system according to claim 1, wherein the injector head assembly comprises the means for adjusting.

3. The MRI system according to claim 2, wherein the injector head assembly comprises a keypad having a plurality of keys for entering commands for controlling operation of the injector head assembly, the means for entering the adjusting command being included in the keypad and the adjusting command consisting of a pre-defined combination of the keys.

4. The MRI system according to claim 1, wherein the MRI system comprises a computing machine configured for controlling operation of the MRI system, the computing machine including the means for adjusting.

5. The MRI system according to claim 4, wherein the means for adjusting comprises a further memory structure storing an indication of one or more known artifacts, the means for detecting the degradation including means for detecting the degradation according to a comparison of the images with the known artifacts.

6. The MRI system according to claim 1, wherein the MRI system comprises means for measuring at least one operative parameter of the injector head assembly and means for validating the new value according to said at least one operative parameter.

7. The MRI system according to claim 6, wherein said at least one operative parameter comprises a frequency of a communication port of the injector head assembly.

8. The MRI system according to claim 6, wherein the MRI system comprises a driving device configured for driving the injector head assembly, the means for measuring being included in the driving device.

9. The MRI system according to claim 1, wherein the memory structure stores a candidate list of the candidate values of the clock frequency.

10. The MRI system according to claim 1, wherein the memory structure stores a candidate range of the clock frequency.

11. The MRI system according to claim 1, wherein the clock frequency has a nominal value with a nominal tolerance, the candidate values being in a nominal range defined by the nominal value and the nominal tolerance.

12. The MRI system according to claim 1, wherein the MRI system comprises means for generating magnetic pulses at a radio frequency, the new value having no harmonic frequencies matching the radio frequency.

13. The MRI system according to claim 1, wherein the clock unit comprises an RC oscillator configured for generating the clock signal and wherein the means for adjusting comprises means for setting the RC oscillator according to the new value of the clock signal.

14. An injector system configured for use in the MRI system according to claim 1, the injector system comprising said injector head assembly including said memory structure, said means for adjusting, and said means for selecting.

15. A computing machine configured for controlling operation of the MRI system according to claim 1, the computing machine including said memory structure, said means for adjusting, and said means for selecting.

16. A method for managing an injector head assembly adapted to inject at least one medical fluid into a patient under analysis in an MRI system adapted to generate one or more images of a body-part of the patient, wherein the injector head assembly comprises a control unit configured for controlling operation of the injector head assembly and a clock unit configured for providing a clock signal with a clock frequency to the control unit (310), the method comprising:

adjusting the clock frequency in an operative condition of the MRI system from a current value to a new value; and selecting the new value among a plurality of candidate values of the clock frequency from an indication thereof stored in a memory structure of the MRI system;

wherein said adjusting the clock frequency includes entering an adjusting command manually and triggering the adjusting of the clock frequency in response to the adjusting command; and/o monitoring the images generated by the MRI system, detecting a degradation of the images according to artifacts thereof and triggering the adjusting of the clock frequency in response to the degradation of the images.

17. The method according to claim 16, wherein the method comprises:

adjusting the clock frequency from the current value to the new value under the control of the injector head assembly.

18. The method according to claim 17, wherein the method comprises:

entering the adjusting command manually with a keypad of the injector head assembly having a plurality of keys for entering commands for controlling operation of the injector head assembly, the adjusting command consisting of a pre-defined combination of the keys of the keypad.

19. The method according to claim 16, wherein the method comprises:

adjusting the clock frequency from the current value to the new value under the control of a computing machine for controlling operation of the MRI system.

20. The method according to claim 19, wherein the method comprises:

detecting the degradation according to a comparison of the images with known artifacts stored in a further memory structure of the MRI system.

21. The method according to claim 16, wherein the method comprises:

measuring at least one operative parameter of the injector head assembly, and validating the new value according to said at least one operative parameter.

22. The method according to claim 21, wherein said measuring at least one operative parameter comprises:

measuring a frequency of a communication port of the injector head assembly.

23. The method according to claim 21, wherein said measuring at least one operative parameter comprises:

measuring said at least one operative parameter by a driving device configured for driving the injector head assembly.

24. The method according to claim 16, wherein the method comprises:
selecting the new value from a list of the candidate values of the clock frequency stored in the memory structure.

25. The method according to claim 16, wherein the method comprises:
selecting the new value from a candidate range of the clock frequency stored in the memory structure.

26. The method according to claim 16, wherein the clock frequency has a nominal value with a nominal tolerance, the candidate values being in a nominal range defined by the nominal value and the nominal tolerance.

27. The method according to claim 16, wherein the MRI system comprises means for generating magnetic pulses at a radio frequency, the new value having no harmonic frequencies matching the radio frequency.

28. The method according to claim 16, wherein said adjusting the clock frequency comprises:
setting an RC oscillator for generating the clock signal according to the new value of the clock signal.

29. A tangible, non-transitory computer-readable medium storing program instructions that, when executed by a computing system, cause the computer system to perform the method according to claim 16.

\* \* \* \* \*